United States Patent [19]

Martel et al.

[11] 4,443,617

[45] Apr. 17, 1984

[54] PROCESS FOR THE PREPARATION OF DERIVATIVES OF 6,6-DIMETHYL-4-HYDROXY-3-OXABICY-CLO-[3,1,0]-HEXAN-2-ONE

[75] Inventors: Jacques Martel, Bondy; Jean Tessier, Vincennes; Jean-Pierre Demoute, Montreuil-sous-Bois, all of France

[73] Assignee: Roussel Uclaf, Paris, France

[21] Appl. No.: 394,457

[22] Filed: Jul. 1, 1982

Related U.S. Application Data

[62] Division of Ser. No. 153,338, May 27, 1980.

[30] Foreign Application Priority Data

Jun. 6, 1979 [FR] France ................................ 79 14425

[51] Int. Cl.$^3$ ............................................. C07D 307/93
[52] U.S. Cl. ..................................... 549/302; 549/313
[58] Field of Search ................................. 549/302, 313

[56] References Cited

U.S. PATENT DOCUMENTS

| | | | |
|---|---|---|---|
| 4,132,717 | 1/1979 | Roman | 549/302 |
| 4,235,780 | 11/1980 | Kondo et al. | 549/302 |
| 4,331,605 | 5/1982 | Martel et al. | 549/302 |
| 4,342,694 | 8/1982 | Kondo et al. | 549/302 |

Primary Examiner—Jane T. Fan
Attorney, Agent, or Firm—Bierman, Bierman, Peroff & Muserlian

[57] ABSTRACT

Novel 3-formyl-4-methyl-pent-3-ene-1-oic acid of the formula

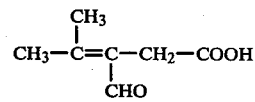

I and a process for its preparation and intermediates and a process for the preparation of compounds of the formula

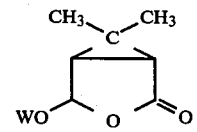

V wherein W is selected from the group consisting of hydrogen and $R_1$ of an optionally chiral alcohol $R_1OH$, useful as an intermediate for the producton of numerous ester having elevated insecticidal activity.

8 Claims, No Drawings

PROCESS FOR THE PREPARATION OF DERIVATIVES OF 6,6-DIMETHYL-4-HYDROXY-3-OXABICYCLO-[3,1,0]-HEXAN-2-ONE

This is a divison of Ser. No. 153,338 pending filed May 27, 1980.

OBJECTS OF THE INVENTION

It is an object of the invention to provide the novel product, 3-formyl-4-methyl-pent-3-ene-1-oic acid, and a novel process for its preparation.

It is another object of the invention to provide a novel process for the preparation of compounds of formula V and novel intermediates produced therein.

These and other objects and advantages of the invention will become obvious from the following detailed description.

THE INVENTION

The novel product of the invention is 3-formyl-4-methyl-pent-3-ene-1-oic acid of the formula

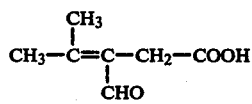

The novel process of the invention for the preparation of 3-formyl-4-methyl-pent-3-ene-1-oic acid comprises reacting a compound of the formula

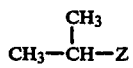

wherein Z is an electro-attractive group with a compound the formula

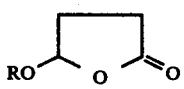

wherein R is the residue of an ROH alcohol to obtain a compound of the formula

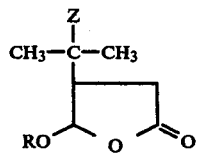

and treating the latter with a basic agent to obtain 3-formyl-4-methyl-pent-3-ene-1-oic acid.

ROH is preferably a straight or branched aliphatic alcohol of 1 to 12 carbon atoms such as, for example methanol, ethanol, propanol, isopropanol, butanol, isobutanol optionally branched pentanol and hexanol, which aliphatic alcohol may further be substituted, for example, by a alkyl or by an optionally substituted heterocyclic or aromatic radical.

When Z is $-NO_2$, the reaction of the compounds of formulae II and III is preferably effected in the presence of a base selected from the group consisting of secondary or tertiary amines, quaternary ammonium hydroxides and alkali metal carbonates. An example of a preferred tertiary amine is triethylamine.

When Z is -OH, the reaction of the compounds of formulae II and III is effected with irradiation or in the presence of a radical promoter. Preferred radical promoter are benzoyl peroxide, azobis-isobutyronitrile, ditert.-butyl peroxide, tert.-butyl perbenzoate and dilauryl peroxide.

When Z is an arylsulfonyl group, the reaction of the compounds of formulae II and III is effected in the presence of a strong base in an organic solvent. A preferred arylsulfonyl group is p-tolylsulfonyl.

When Z is a triarylphosphonic halo group, the reaction of the compounds of formulae II and III is effected in the presence of a strong base in an organic solvent. A preferred triarylphosphonio halo group is triphenyl phosphonio iodo.

In the latter 2 cases for Z, the strong base is preferably selected from the group consisting of alkyllithiens, alkali metal amides, alkali metal hydrides and alkali metal alcoholates and the organic solvent is selected from the group consisting of tetrahydrofuran, dimethylformamide, dimethylsulfoxide, dimethoxyethane, hexamethylphosphoramide, aromatic hydrocarbons and cycloalkanes. The most preferred conditions are in the presence of butyllithium in a mixture of tetrahydrofuran and cyclohexane.

The basic agent used to treat the compound of formula IV may be an alkali metal carbonate in an aqueous media such as sodium carbonate in aqueous methanol.

Another facet of the invention comprises a process for the preparation of a compound of the formula

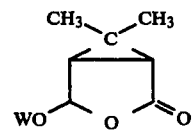

wherein W is selected from the group consisting of hydrogen and $R_1$ is derived from an optionally chiral alcohol $R_1OH$ comprising reacting 3-formyl-4-methyl-pent-3-ene-1-oic acid under anhydrous conditions with a hydrogen halide in the presence of LiX wherein X is a halogen in an organic solvent to obtain a compound of the formula

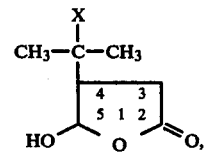

reacting the latter with an achiral alcohol $R_1OH$ to obtain a racemic compound of the formula

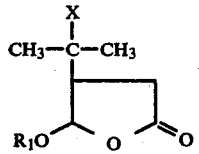

which, together with the compound of formula VI has a trans relationship with the 4 and 5 substituents of the tetrahydrofuranone or with a chiral alcohol $R_1OH$, compound VII will be a mixture of the predictable diastereoisomers which may be separated into the individual isomers by physical methods and then reacting the compound of formula VII in its racemic form when $R_1$ is achiral or in the form of one of its optically active isomers wherein $R_1$ is chiral with a basic agent to obtain the bicyclic compound of the formula

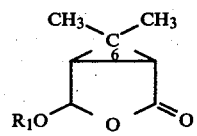

V' in its racemic form or one of its 2 enantiomeric forms when $R_1$ is an achiral or a chiral group, respectively, the absolute configuration of the 4-position as well as the following 1- and 5-positions being determined by the stereochemistry of the diasteroisomer of formula VII and optionally subjecting the compound of formula V' to hydrolysis in an acid medium with total retention of the absolute configurations to obtain a compound of the formula

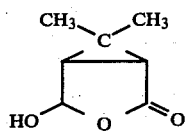

V"

In a preferred mode of the latter process of the invention, the reaction of 3-formyl-4-methyl-pent-3-ene-1-oic acid is effected with HBr/LiBr or HCl/LiCL couple in anhydrous ethyl ether and the reaction of the compound of formula VI with an achiral or a chiral alcohol $R_1OH$ is effected in the presence of p-toluene sulfonic acid.

The two diastereoisomers produced where $R_1OH$ is a chiral alcohol with the racemate of formula VI may be separated by chromatography as well as by crystallization. The basic agent reacted with the compound of formula VII is preferably butyllithium but the reaction may also be effected either by the method of phase transfer catalysis with an alkali metal hydroxide, water, a non-water miscible solvent and a quaternary ammonium compound or with sodium hydride. In the latter catalytic method, the alkali metal hydroxide is preferably sodium hydroxyde.

The hydrolysis of the compounds of formula V' is preferably effected with hydrochloric acid in an aqueous acetone medium although other acids may be used.

$R_1OH$ is chiral or achiral and is preferably a straight or branched aliphatic alcohol of 1 to 12 carbon atoms such as, for example, methanol, propanol, isopropan butanol, isobutanol and optionally branched pentanol and hexanol, which aliphatic alcohol may further be substituted for example, by a halogen or by an optionally substituted heterocyclic or aromatic radical.

Semisynthetic methods are known for the preparation of 6,6-dimethyl-4-hydroxy-3-oxabicyclo-[3,1,0]-hexan-2-one starting from the very elaborate compound, chrysanthemic acid such as French Pat. No. 1,580,474. The process of the present invention permits the total synthesis of 6,6-dimethyl-4-hydroxy-3-oxabicyclo-[3,1,0]-hexan-2-one and its ethers in racemic form or in the form of its optically active isomers, starting from 3-formyl-4-methyl-pent-3-ene-1-oic and using readily available reactants and a limited number of steps.

The said total synthesis of compounds such as 6,6-dimethyl-4-hydroxy-3-oxabicyclo-[3,1,0]-hexan-2-one is of particularly remarkable interest since it is a valuable intermediate for the synthesis of numerous esters having elevated insecticidal activity as described in French Pat. No. 2,185,612.

The novel intermediates of the invention are those of the formulae

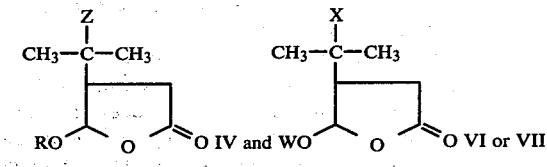

wherein Z is an electro-attractive group, R is the residue of an ROH alcohol, X is a halogen and W is selected from the group consisting of hydrogen and $R_1$, $R_1$ is derived from an optionally chiral alcohol $R_1OH$. Preferably, X is chlorine or bromine and Z is —OH, —NO$_2$, p-tolylsulfonyl or a triphenylphosphonio halo group.

In the following examples there are described several preferred embodiments to illustrate the invention. However, it should be understood that the invention is not intended to be limited to the specific embodiments.

EXAMPLE 1

3-formyl-4-methyl-pent-3-ene-1-oic acid

STEP A: Trans dl 4-(2-nitro-prop-2-yl)-5-methoxy-tetrahydrofuran-2-one

A mixture of 9 ml of 2-nitropropane, 7 g of 5-methoxy-2,5-dihydrofuran-2-one-3-ene and 1 ml of triethylamine was stirred at 20°–25° C. for 70 hours and the mixture was then washed with an aqueous monosodium phosphate solution and was extracted with benzene. The organic phase was dried and evaporated to dryness under reduced pressure and the residue was taken up in isopropyl ether. Crystallization was induced and the mixture was cooled to 0° C. with stirring and was vacuum filtered to obtain 8.42 g of trans dl 4-(2-nitro-prop-2-yl)-5-methoxytetrahydrofuran-2-one melting at $\simeq$33° C.

Analysis: $C_8H_{13}NO_5$; molecular weight=203.18. Calculated: %C, 47.29; %H, 6.45; %N, 6.89. Found: %C, 47.10; %H, 6.50; %N, 6.70.

NMR Spectrum (CDCl$_3$-60 MHz): Peaks at 1.6 ppm (hydrogens of geminal methyls); at 2.0–3.17 ppm (3- and 4-hydrogens of cyclopentyl); at 3.5 ppm (hydrogens of CH$_3$O—).

STEP B: 3-formyl-4-methyl-pent-3-ene-1-oic acid

A solution of 18.2 g of the product of Step A in 25 ml of methanol were added all at once to a solution of 18.9 g of sodium carbonate in 180 ml of water cooled to 0° C. and the mixture stood at room temperature for 120 hours. The mixture was washed with ether and cooled to 0° C. after which concentrated sulfuric acid was added to the mixture under an inert atmosphere until the pH was $\simeq$1. The mixture was extracted with chloroform and then with ethyl acetate and the combined organic phases were dried and evaporated to dryness under reduced pressure to obtain 9.5 g of residue. The latter was crystallized from water to obtain 7.4 g of pure 3-formyl-4-methyl-pent-3-one-1-oic acid melting at 102° C.

Analysis: $C_7H_{10}O_3$; molecular weight=142.156. Calculated: %C, 59.14; %H, 7.09. Found: %C, 59.20; %H, 7.0.

NMR Spectrum (CDCl$_3$-60 MHz): Peaks at 2.0 ppm (5-hydrogen); at 2.26 ppm (hydrogens of 4-CH$_3$); at 3.38 ppm (2-hydrogens); at 10.13 ppm (hydrogen of formyl).

EXAMPLE 2

3-formyl-4-methyl-pent-3-ene-1-oic acid

STEP A:
5-(3-phenoxyphenyl)-methoxy-2,5-dihydrofuran-2-one

A mixture of 12 g of 5-hydroxy-2-(5H)-furanone, 250 ml of benzene, 25 g of m-phenoxy-benzyl alcohol and 200 mg of p-toluene sulfonic acid was stirred while benzene was distilled with the benzene being replaced four times with an equal volume of dry benzene. After 2 hours, the mixture was cooled to room temperature and was washed with aqueous saturated sodium bicarbonate solutiion and then with water, dried and evaporated to dryness under reduced pressure. The 39.7 g of oil were chromatographed over silica gel and was eluted with a 9-1 benzene-ethyl acetate mixture to obtain 24.9 g of 5-(3-phenoxyphenyl)-methoxy-2,5-dihydrofuran-2-one.

NMR Spectrum (CDCl$_3$-60 MHz): Peaks at 7.3–7.4 ppm (4-hydrogens of furanone); at 6.18–6.32 ppm (3-hydrogens of furanone); at 6.03 ppm (5-hydrogen of furanone); at 4.58–4.76 ppm and 4.85–5.12 ppm (hydrogens of CH$_3$O—); at 6.92–7.5 ppm (aromatic ring).

STEP B: Trans dl
4-(2-hydroxy-prop-2-yl)-5-(3-phenoxyphenyl)-methoxy-tetrahydrofuran-2-one A mixture of 3.5 g of the product of Step A in 100 ml of isopropanol was refluxed with stirring under an inert atmosphere while regularly adding over 90 minutes, 300 mg of benzoyl peroxide in 25 mg portions and the mixture was evaporated to dryness under reduced pressure at 40° to 50° C. The residue was chromatographed over silica gel and was eluted with an 8-2 benzene-ethyl acetate mixture to obtain 3.7 g of raw product which which was crystallized from isopropyl ether to obtain trans dl 4-(2-hydroxy-prop-2-yl)-5-(3-phenoxyphenyl)-methoxy-tetrahydrofuran-2-one in the form of white crystals melting at 50°–55° C.

Analysis: $C_{20}H_{22}O_3$; molecular weight=342.39. Calculated: %C, 70.16; %H, 6.4. Found: %C, 69.9; %H, 6.5.

NMR Spectrum (CDCl$_3$-60 MHz): Peaks at 1.18 and 1.21 (hydrogens of methyls); at 2.16–2.75 ppm (3- and 4-hydrogens of cyclopentyl); at 4.48–4.35 ppm and 4.8–5 ppm (hydrogens of benzylic methylene); at 5.59–5.58 ppm (5-hydrogens of cyclopentyl); at 6.83–7.5 ppm (aromatic ring); at 1.5 ppm (hydrogen of OH).

STEP C: 3-formyl-4-methyl-pent-3-ene-1-oic acid 1 g of the product of Step B and 2 ml of methanol were added with stirring at 0° C. to a solution of 619 mg of sodium carbonate in 6 ml of water and the mixture stood at room temperature for 19 hours. The mixture was washed with ether and cooled to 0° C. and then concentrated sulfuric acid was slowly added thereto until the pH was 1. The mixture was extracted with methanol and then with chloroform and the combined organic phases were dried and evaporated to dryness under reduced pressure to obtain 245 g of raw residue which was crystallized to obtain 3-formyl-4-methyl-pent-3-ene-1-oic acid melting at 102° C.

EXAMPLE 3

3-formyl-4-methyl-pent-3-ene-1-oic acid

STEP A: Trans dl
4-(2-p-toluenesulfonyl-prop-2-yl)-5-methoxy-tetrahydrofuran-2-one 1.3 ml of a cyclohexane solution of 1.95 M of butyllithium was slowly added with stirring at −70° C. under an inert atmosphere to a mixture of 500 mg of isopropyl-p-tolyl sulfone and 10 ml of anhydrous tetrahydrofuran and the mixture was stirred at −70° C. for 30 minutes. A solution of 287 mg of 5-methoxy-2,5-dihydrofuran-2-one in 4 ml of tetrahydrofuran was added to the mixture over 10 minutes and the mixture was held at −70° C. for one hour and was then poured into aqueous monosodium phosphate solution at 0° C. The mixture was extracted with methylene chloride and the organic phase was washed with water, dried and evaporated to dryness under reduced pressure. The residue was crystallized from isopropyl ether to obtain 490 mg of trans dl 4-(2-p-toluenesulfonyl-prop-2-yl)-5-methoxy-tetrahydrofuran-2-one in the form of white crystals melting at 129° C.

Analysis: Calculated: %C, 57.67; %H, 6.45; %S, 10.26. Found: %C, 57.6; %H, 6.5; %S, 10.1.

NMR Spectrum (CDCl$_3$-60 MHz): Peaks at 1.27–1.32 ppm (hydrogens of geminal methyls); at 2.46 ppm (hydrogens of methyl in aromatic ring); 2.75 ppm (3- and 4-hydrogens of cyclopentyl); at 5.58 ppm (5-hydrogen of cyclopentyl); at 3.51 ppm (hydrogens of CH$_3$O—); at 7.28–7.42 ppm (3- and 5-hydrogens of aromatic ring); at 7.66–7.8 ppm (2- and 6-hydrogens of aromatic ring).

STEP B: 3-formyl-4-methyl-pent-3-ene-1-oic acid

A mixture of 250 mg of the product of Step A, 4 ml of water, 0.8 ml of methanol and 250 mg of sodium carbonate was stirred for 2 hours at room temperature and the mixture was washed with ether. The aqueous phase was adjusted to a pH of 3-3.5 by addition of N hydrochloric acid and was then saturated with sodium chloride. The mixture was extracted with chloroform and the organic phase was dried and evaporated to dryness under reduced pressure to obtain 87 mg of 3-formyl-4-methyl-pent-3-ene-1-oic acid melting at 102° C. which was identical in all aspects with the product obtained by another method.

EXAMPLE 4

3-formyl-4-methyl-pent-3-ene-1-oic acid

STEP A:
[1-(5-methoxy-2-oxo-4,5-dihydro-3H-furan-4-yl)-1-methyl-1-ethyl]-triphenylphosphonium iodide 3.5 ml of a solution of 2 M butyllithium in cyclohexane were added all at once to a suspension of 3 g of triphenyl isopropyl phosphonium iodide in 40 ml of tetrahydrofuran and the mixture was stirred at room temperature for 10 minutes to obtain a solution of an ylide. A solution of 0.800 g of 5-methoxy-2,5-dihydrofuran-2-one-3-ene in 50 ml of tetrahydrofuran cooled to −60° C. was slowly added under an inert atmosphere to the ylide solution cooled to −60° C. and the mixture was stirred for 10 minutes and was poured into a mixture of ice and aqueous monosodium phosphate solution. The mixture was washed with ether and was extracted with methylene chloride. The organic extract was dried and evaporated to dryness under reduced pressure to obtain 3.4 g of [1-(5-methoxy-2-oxo-4,5-dihydro-3H-furan-4-yl)-1-methyl-1-ethyl]-triphenyl-phosphonium iodide melting towards 140° C.

Analysis: $C_{26}H_8IO_3P$; molecular weight = 546.37. Calculated: %C, 57.15; %H, 5.16; %I, 22.24; %P, 5.67. Found: %C, 57.3; %H, 5.2; %I, 22.4; %P, 5.3.

NMR Spectrum (CDCl$_3$-60 MHz): Peaks at 1.63-1.80-1.95-2.10 ppm (hydrogens of methyls β to phosphorus); at 2.22-3.33 ppm (hydrogens on 3- and 4-carbons of furanone); at 3.23 ppm (hydrogens of CH$_3$O—); at 5.46-5.54 ppm (5-hydrogen of furanone); at 7.81-7.92 ppm (hydrogens of aromatic ring).

STEP B: 3-formyl-4-methyl-pent-3-ene-1-oic acid

A solution of 0.700 g of sodium carbonate in 8 ml of water was added to a solution of 0.700 g of the product of Step A in 1 ml of methanol and the mixture was stirred for 2 hours at 20° C. and was filtered. The filtrate was adjusted to a pH of 2 and was saturated with sodium chloride. The mixture was extracted with chloroform and the organic phase was evaporated to dryness. The residue was crystallized from isopropyl ether to obtain 0.095 g of 3-formyl-4-methyl-pent-3-ene-1-oic acid melting at 102°L C.

EXAMPLE 5

(dl) 6,6-dimethyl-4-hydroxy-3-oxa-bicyclo [3,1,0]-hexan-2-one

STEP A: dl trans 4-(2-chloro-prop-2-yl)-5-hydroxy-tetrahydrofuran-2-one

A mixture of 1 g of 3-formyl-4-methyl-pent-3-ene-1-oic acid, 25 ml of anhydrous ether and 1 g of lithium chloride was stirred under a current of gaseous hydrogen chloride at —30° C. for 2 hours and then for 2 hours at 0° C. after which the gaseous hydrogen chloride was shut off. The mixture was stirred at room temperature for 48 hours and after 54 hours of contact, the mixture was poured into iced water. The decanted aqueous phase was extracted with benzene and the organic phase was dried and evaporated to dryness under reduced pressure. The 1.1 g of residue was chromatographed over silica gel and was eluted with a 1-1 benzene-ethyl acetate mixture to obtain 545 mg of crystalline (dl trans 4-(2-chloro-prop-2-yl)-5-hydroxy-tetrahydrofuran-2one melting at 80° C.

Analysis: $C_7H_{11}ClO_3$; molecular weight = 178.617. Calculated: %C, 47.07; %H, 6.21; %Cl, 19.85. Found: %C, 47.2; %H, 6.2; %Cl, 19.5.

NMR Spectrum (CDCl$_3$-60 MHz): Peaks at 1.55 and 1.66 ppm (hydrogens of methyls); at 2.42-2.92 ppm (3- and 4-hydrogens of ring); at 5.82-5.89 ppm (5-hydrogen of ring); at 3.83 ppm (hydrogen of OH).

STEP B: 4-(2-chloro-prop-2-yl)-5-[3-phenoxyphenyl-methoxy]-tetrahydrofuran-2-one A mixture of 393 mg of the product of Step B, 668 mg of m-phenoxybenzyl alcohol, 20 mg of p-toluene sulfonic acid and 5 ml of benzene was stirred for 19 hours at room temperature and the mixture was neutralized with a little sodium bicarbonate, dried and evaporated to dryness under reduced pressure. The 1.18 g of residue was chromatographed over silica gel and was eluted with benzene to obtain 467 mg of 4-(2-chloro-prop-2-yl)-5-[3-phenoxyphenyl-methoxy]-tetrahydrofuran-2-one which after crystallization from petroleum ether melted at 50° C.

Analysis: $C_{20}H_{21}ClO_4$; molecular weight = 360.84. Calculated: %C, 66.57; %H, 5.87; %Cl, 9.83. Found: %C, 66.60; %H, 5.80; %Cl, 9.90.

NMR Spectrum (CDCl$_3$-60 MHz): Peaks at 1.5 and 1.55 ppm (hydrogens of methyls); at 2.55-2.72 ppm (3- and 4-hydrogens of cyclopentyl); at B 5.52-5.56 ppm (5-hydrogen of cyclopentyl); at 4.47-4.66 ppm and 4.77-4.97 ppm (hydrogens of benzylic methylene); 6.92-7.5 ppm (aromatic hydrogens).

STEP C: dl 6,6-dimethyl-4-hydroxy-3-oxabicyclo-[3,1,0]-hexan-2-one 0.25 ml of a solution of 2 M butyllithium in cyclohexane was added at —20° C. to 0.55 ml of a molar solution of diisopropylamine in tetrahydrofuran and 5 ml of tetrahydrofuran and the temperature was allowed to rise to 0° C. and was then cooled to —60° to —70° C. 180 mg of the product of Step B were added all at once to the mixture at —60° to —70° C. and the mixture was heated over 2 hours at 0° C. The mixture was held at 0° C. for one hour and was poured into 2 N hydrochloric acid. The mixture was stirred for 17 hours at 20° C. and the decanted aqueous phase was extracted with chloroform. The organic phase was dried and evaporated to dryness and the residue was taken up in a mixture of isopropyl ether and petroleum ether. The solution was extracted with water and the aqueous extract was evaporated to dryness under reduced pressure to obtain 30 mg of crystalline dl 6,6-dimethyl-4-hydroxy-3-oxabicyclo-[3,1,0]-hexan-2-one melting at 80° C.

EXAMPLE 6 dl 6,6-dimethyl-4-hydroxy-3-oxabicyclo-[3,1,0]-hexan-2-one

STEP A: dl trans 4-(2-bromo-prop-2-yl)-5-hydroxy-tetrahydrofuran-2-one

A mixture of 2.35 g of 3-formyl-4-methyl-pent-3-ene-1-oic acid, 2.7 g of dry lithium bromide and 60 ml of anhydrous ether was stirred at —35° C. for 90 minutes while bubbling gaseous hydrogen bromide therethrough and then a strong current of nitrogen was bubbled therethrough at —30° to —40° C. The mixture was poured into iced water and was extracted with benzene. The organic phase was dried and evaporated to dryness under reduced pressure without heating to obtain 3.27 g of an oil which crystallized and which was then crystallized from petroleum ether to obtain 2.5 g of dl trans 4-(2-bromo-prop-2-yl)-5-hydroxy-tetrahydrofuran-2-one in the form of white crystals melting at ≃75° C.

Analysis: $C_7H_{11}BrO_3$; molecular weight = 223.073. Calculated: %C, 37.69; %H, 4.97; %Br, 35.82. Found: %C, 37.80; %H, 5.20; %Br, 35.20.

NMR Spectrum (CDCl$_3$-60 MHz): Peaks at 1.74 and 1.86 ppm (hydrogens of methyls); at B 2.25-3.0 ppm (3- and 4-hydrogens of ring); at 5.87 and 5.93 ppm (5-hydrogen of ring); at 3.92 ppm (hydrogen of hydroxyl).

STEP B:
4-(2-bromo-prop-2-yl)-5-[3-phenoxyphenyl-methoxy]-tetrahydrofuran-2-one A mixture of 5.5 g of the product of Step A, 5.2 g of m-phenoxy-benzyl alcohol, 50 ml of benzene and 270 mg of p-toluene sulfonic acid was stirred for 24 hours at room temperature and the mixture was washed with aqueous sodium bicarbonate solution and was extracted with benzene. The organic phase was dried and evaporated to dryness under reduced pressure to obtain 10 g of oil which crystallized. The product was crystalized from a 7-5 isopropyl ether-petroleum ether to obtain 5.83 g of 4-(2-bromo-prop-2-yl)-5-[3-phenoxyphenyl-methoxy]-tetrahydrofuran-2-one melting at 60° C. Chromatography of the mother liquors yielded another 1 g of the product of the same purity.

Analysis: $C_{20}H_{21}BrO_4$. Calculated: %C, 59.27; %H, 5.22; %Br, 19.72. Found: %C, 60.10; %H, 5.60; %Br, 21.50.

NMR Spectrum (CDCl$_3$-60 MHz): Peaks at 1.67-1.7 ppm (hydrogens of methyls); at 2.22-2.92 ppm (3- and 4-hydrogens of cyclopentyl); at 5.53-5.58 ppm (5-hydrogen of cyclopentyl); at 4.48-4.68 ppm and 4.78-4.98 ppm (hydrogens of benzylic methylene); at 6.92-7.58 ppm (hydrogens of aromatic ring).

STEP C: dl
6,6-dimethyl-4-hydroxy-3-oxabicyclo-[3,1,0]-hexan-2-one 0.25 ml of a solution of 2 M n-butyllithium in cyclohexane was added at −20° C. to 0.55 ml of a molar solution of diisopropylamine in tetrahydrofuran and 5 ml of tetrahydrofuran and the mixture was heated to 0° C. and was cooled to −60° C. 200 mg of the product of Step B were added all at once to the mixture at −60° C. and the mixture was held at −60° C. for 15 minutes and then was poured into iced 2 N hydrochloric acid solution. The mixture was stirred at 20° C. for 17 hours and the decanted aqueous phase was extracted with chloroform. The organic phase was dried and evaporated to dryness to obtain 170 mg of residue. The residue was taken up in a mixture of isopropyl ether and petroleum ether and the organic phase was washed with water. The aqueous phase was evaporated to dryness under reduced pressure to obtain 50 mg of crystalline dl 6,6-dimethyl-4-hydroxy-3-oxabicyclo-[3,1,0]-hexan-2-one melting at 80° C.

EXAMPLE 7
6,6-dimethyl-4-hydroxy-3-oxabicyclo-[3,1,0]-hexan-2-one

STEP A: A and B isomers of trans 4-(2-bromo-prop-2-yl)-5-[(3-phenoxyphenyl)-methyl-methoxy]-tetrahydrofuran-2-one A mixture of 6.07 g of dl trans 4-(2-bromo-prop-2-yl)-5-hydroxy-tetrahydrofuran-2-one, 5.83 g of (S)α-methyl-3-phenoxy-benzyl alcohol, 300 mg of p-toluene sulfonic acid, 60 ml of benzene and 10 g of colored Actigel deshydratant was stirred at 20°-25° C. for 24 hours and the reaction mixture was washed with aqueous sodium bicarbonate solution. The mixture was extracted with benzene and the organic phase was dried and evaporated to dryness under reduced pressure to obtain 9.5 g of residue. The residue was chromatographed over silica gel and was eluted with methylene chloride to obtain 5 g of A and B isomers of trans 4-(2-bromo-propy-2-yl)-5-[(3-phenoxyphenyl)-methyl-methoxy]-tetrahydrofuran-2-one. Crystallization from isopropyl ether containing 30% of petroleum ether yielded 960 mg of the B isomer melting at ≃76° C. and having a specific rotation of $[\alpha]_D^{20} = +188.5°$ (c=1% in benzene). Chromatography of the mother liquors over silica gel and elution with methylene chloride obtained the A isomer in the form of an oil.

STEP B: (1R,5S) 6,6-dimethyl-4(R) [(S)(3-phenoxybenzyl)-methoxy]-3-oxabicyclo-[3,1,0]-hexan-2-one A mixture of 300 mg of the B isomer of Step A, 3 ml of methylene chloride, 3 ml of a 50% aqueous sodium hydroxide solution and 30 mg of triethylbenzyl ammonium chloride was stirred at room temperature for 2½ hours and was then poured into an iced aqueous monosodium phosphate solution. The mixture was extracted with methylene chloride and the organic phase was washed with water, dried and evaporated to dryness under reduced pressure. The 221 mg of residue crystallized and was then crystallized from 4 ml of a 7-3 petroleum ether-isopropyl ether mixture to obtain 165 mg of white (1R, 5S) 6,6-dimethyl-4(R)-[(S)(3-phenoxybenzyl)-methoxy]-3-oxabicyclo-[3,1,0]-hexan-2-one with a melting point ≃110° C. Chromatography of the mother liquor yielded another 17 mg of the product. The form of white crystals melting at ≃110° C. The product had a specific rotation of $[\alpha]_D^{20} = -241°$ (c=1% in benzene).

NMR Spectrum (CDCl$_3$-60 MHz): Peaks at 1.1 and 1.13 ppm (hydrogens of geminal methyls); at 2.03 ppm (1- and 5-hydrogens); at 4.96 ppm (4-hydrogen); at 1.42 and 1.53 ppm (hydrogens of methyl fixed on benzyl carbon); at 4.7-4.8-4.9 and 5.0 ppm (hydrogen on benzylic carbon); at 6.83-7.5 ppm (hydrogens of aromatic ring).

STEP C: (1R,5S) 6,6-dimethyl-4-hydroxy-3-oxabicyclo-[3,1,0]-hexan-2-one

A mixture of 1 g of the product of Step B, 10 ml of acetone and 5 ml of aqueous N hydrochloric acid was stirred at 20°-25° C. for 2 hours and the pH of the mixture was adjusted to 8 by addition of sodium bicarbonate. The mixture was washed with methylene chloride and the pH of the mixture was adjusted to 1 by addition of concentrated hydrochloric acid. The mixture was extracted with ethyl acetate and the organic phase was dried and evaporated to dryness under reduced pressure to obtain 384 mg of crystalline (1R,5S) 6,6-dimethyl-4-hydroxy-3-oxabicyclo-[3,1,0]-hexan-2-one melting at 117° C. The product was identical to that of French patent No. 1,580,474 and had a specific rotation of $[\alpha]_D^{20} = -110°$ C. (c=1% in dimethylformamide).

EXAMPLE 8
dl 6,6-dimethyl-4-hydroxy-3-oxabicyclo-[3,1,0]-hexan-2-one

STEP A: dl trans 4-(2-bromo-prop-2-yl)-5-isopropyloxy-tetrahydrofuran-2-one A mixture of 1.95 g of dl trans 4-(2-bromo-prop-2-yl)-5-hydroxy-tetrahydrofuran-2-one, 2 ml of isopropanol, 100 mg of p-toluene sulfonic acid and 30 ml of benzene was stirred at room temperature for 60 hours and was then washed with aqueous sodium bicarbonate solution. The mixture was extracted with benzene and the organic phase was dried and evaporated to dryness under reduced pressure to obtain 2 g of dl trans 4-(2-bromoprop-2-yl)-5-isopropyloxy-tetrahydrofuran-2-one as an oily product which was used as is for the next step.

STEP B: dl 6,6-dimethyl-4-isopropyl-3-oxabicyclo-[3,1,0]-hexan-2-one 150 mg of sodium hydride were added all at once at 0° C. to a mixture of 728 mg of product of Step A, 5 ml of anhydrous tetrahydrofuran and 1 ml of anhydrous dimethylsulfoxide and it was stirred at room temperature for 20 hours under an inert atmosphere. The mixture was poured into aqueous monosodium phosphate solution and was extracted with benzene. The organic phase was dried and evaporated to dryness under reduced pressure to obtain 450 mg of residue. The residue was chromatographed over silica gel and was eluted with a 7-3 petroleum ether-ether mixture to obtain 350 mg of dl 6,6-dimethyl-4-isopropyl-3-oxabicyclo-[3,1,0]-hexan-2-one.

NMR Spectrum (CDCl$_3$-60 MHz): Peaks at 1.17–1.31 ppm (hydrogens of 6-methyls and methyls of isopropyl); at 2.02 ppm (1- and 5-hydrogens of ring); at 5.25 ppm (4-hydrogen of ring); at 4.03 ppm (2-hydrogen of propyl).

STEP C: dl 6,6-dimethyl-4-hydroxy-3-oxabicyclo-[3,1,0]-hexan-2-one

A mixture of 150 mg of the product of Step B, 3 ml of acetone and 1 ml of N hydrochloric acid was stirred at 20°-25° C. for 4 hours and the mixture was saturated with sodium chloride. The mixture was extracted with methylene chloride and the organic phase was dried and was evaporated to dryness under reduced pressure to obtain 95 mg of dl 6,6-dimethyl-4-hydroxy-3-oxabicyblo-[3,1,0]-hexan-2-one in the form of white crystals melting at 80° C.

Various modifications of the products and processes of the invention may be made without departing from the spirit or scope thereof and it should be understood that the invention is intended to be limited only as defined in the appended claims.

We claim:

1. A process for the preparation of a compound of the formula

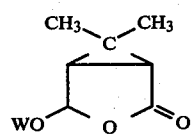

wherein W is selected from the group consisting of hydrogen and R$_1$ is derived from an optionally aliphatic chiral alcohol of 1 to 12 carbon atoms optionally substituted with halogen, aryl or heterocycle consisting essentially of reacting 3-formyl-4-methyl-pent-3-ene-1-oic acid under anhydrous conditions with a hydrogen halide in the presence of LiX wherein X is halogen in an organic solvent to obtain a compound of the formula

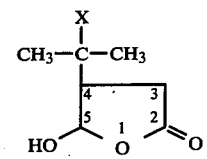

reacting the latter with an achiral alcohol R$_1$OH to obtain a racemic compound of the formula

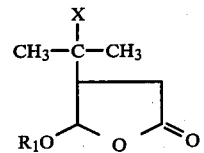

which, together with the compound of formula VI has a trans relationship with the 4 and 5 substituents of the tetrahydrofuranone or with a chiral alcohol R$_1$OH, compound VII will be a mixture of two predictable diastereoisomers which may be separated into the individual isomers by physical methods and then reacting the compound of formula VII in its racemic form when R$_1$ is achiral or in the form of one of its optically active isomers where R$_1$ is chiral with a basic agent to obtain the bicyclic compound of the formula

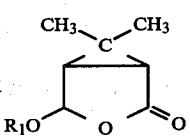

in its racemic form or one of its 2 enantiomeric forms when R$_1$ is an achiral or a chiral group, respectively, the absolute configuration of the 4-position as well as the following 1- and 5-positions being determined by the stereochemistry of the diastereoisomer of formula VII and optionally subjecting the compound of formula V' to hydrolysis in an acid medium with total retention of the absolute configurations to obtain a compound of the formula

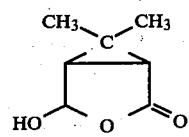

2. The process of claim 1 wherein 3-formyl-4-methyl-pent-3-ene-1-oic acid is reacted with HBr/LiBr or HCl/LiCl in anhydrous ether.

3. The process of claim 1 wherein the compound of formula VI is reacted with R$_1$OH in the presence of p-toluene sulfonic acid.

4. The process of claim 1 wherein the two diastereoisomers due to achiral alcohol R$_1$OH in racemate of formula VI are separated by chromatography or crystallization.

5. The process of claim 1 wherein the transformation of the compound of formula VII is effected with butyllithium.

6. The process of claim 1 wherein the transformation of the compound of formula VII is effected by a method of phase transfer catalysis with an alkali metal hydroxide, water, a non-water miscible solvent and a quaternary ammonium compound.

7. The process of claim 1 wherein the transformation of the compound of formula VII is effected with sodium hydride.

8. The process of claim 1 wherein the hydrolysis is effected with hydrochloric acid in aqueous acetone.

* * * * *